US008670121B1

United States Patent
Pastel et al.

(10) Patent No.: US 8,670,121 B1
(45) Date of Patent: Mar. 11, 2014

(54) WAVELENGTH-TUNABLE DETECTOR FOR LABEL-INDEPENDENT OPTICAL READER

(75) Inventors: David Andrew Pastel, Horseheads, NY (US); Cameron John Tovey, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/613,974

(22) Filed: Sep. 13, 2012

(51) Int. Cl.
*G01N 21/25* (2006.01)

(52) U.S. Cl.
USPC ............................................. 356/416

(58) Field of Classification Search
USPC ............................................. 356/416
See application file for complete search history.

(56) References Cited

U.S. PATENT DOCUMENTS

| 7,239,395 | B2 | 7/2007 | Gollier |
| 7,599,055 | B2 | 10/2009 | Gollier et al. |
| 8,111,401 | B2 * | 2/2012 | Magnusson et al. ......... 356/480 |
| 8,384,905 | B2 * | 2/2013 | Wu ............................. 356/445 |
| 8,514,391 | B2 * | 8/2013 | Wawro et al. ................ 356/300 |
| 2009/0138205 | A1 | 5/2009 | Gollier et al. |
| 2011/0109909 | A1 | 5/2011 | Wu |

OTHER PUBLICATIONS

Gat; "Imaging Spectroscopy Using Tunable Filters: A Review"; Proc. SPIE; vol. 4056; pp. 50-64; 2000.

* cited by examiner

*Primary Examiner* — Tu Nguyen
(74) *Attorney, Agent, or Firm* — John L. Haack

(57) ABSTRACT

A wavelength-tunable detector for use in a label-independent optical reader for reading at least one resonant waveguide grating (RWG) biosensor is disclosed. The wavelength-tunable detector includes a tunable wavelength filter. Broadband light is made incident upon the RWG biosensor to produce resonantly reflected light, which is then passed through the tunable wavelength filter whose central wavelength is adjusted, such as by varying the filter angle of the tunable wavelength filter. This generates filtered resonantly reflected light, which is detected by a photodetector that generates an electrical signal in response thereto. The electrical signal is representative of the detected spectrum, which includes the center resonant wavelength of the RWG biosensor. A controller can be used to determine the center resonant wavelength from the electrical signal.

20 Claims, 3 Drawing Sheets

WAVELENGTH-TUNABLE DETECTOR FOR LABEL-INDEPENDENT OPTICAL READER

The entire disclosure of any publication or patent document mentioned herein is incorporated by reference, including commonly owned and assigned: U.S. 2009/0138205, U.S. 2011/0109909, U.S. Pat. No. 7,239,395, and U.S. Pat. No. 7,599,055.

FIELD

The present disclosure relates to label-independent optical readers, and in particular to wavelength-tunable detectors for use with such readers.

BACKGROUND

Label-independent-detection (LID)-based optical readers can be used, for example, to detect drug binding to a target molecule such as a protein, or changes in living cells as material is displaced within a cell in response to a drug. Certain types of LID optical readers measure changes in refractive index on the surface of a resonant waveguide grating (RWG) biosensor for an array of RWG biosensors. The individual RWG biosensors are located in respective wells of a microplate.

One type of LID optical reader employs a narrowband light source, wherein narrow-band light (i.e., on the order of the resonance reflectance linewidth of the RWG biosensor) is directed to each RWG biosensor using a narrow-band tunable light source. The interrogation light is swept over a range of wavelengths to determine the center resonance wavelength of the RWG biosensors. However, alternative approaches where the RWG biosensors are illuminated with broadband light are desirable.

SUMMARY

In an embodiment, the disclosure is directed to a wavelength-tunable detector for measuring a center resonance wavelength of at least one RWG biosensor having a center resonance wavelength and illuminated with broadband light. The detector includes a tunable wavelength filter having a tunable center wavelength within a tunable center-wavelength range, and a transmission spectrum with a spectral bandwidth narrower than the tunable center-wavelength range. The tunable wavelength filter is arranged to receive and filter the resonantly reflected broadband light to form filtered resonantly reflected light as the tunable center wavelength is adjusted. The detector also includes a photodetector arranged to receive the filtered resonantly reflected light and generate an electrical signal representative of a detected spectrum as a function the tunable center wavelength, wherein the detected spectrum has a center wavelength substantially the same as the RWG biosensor center resonance wavelength.

In another embodiment, the disclosure is directed to a label-independent optical reader for reading at least one RWG biosensor supported by a microplate. The label-independent optical reader includes the wavelength-tunable detector as described above, and a broadband light source that emits the broadband light. The label-independent optical reader also includes an optical system configured to direct the broadband light to the at least one RWG sensor to form the resonantly reflected light, and direct the resonantly reflected light to the wavelength-tunable detector. The label-independent optical reader also includes a controller adapted to receive and process the electrical signal from the photodetector to determine the center resonance wavelength of the at least one RWG biosensor.

In another embodiment, the disclosure is directed to a method of reading at least one RWG biosensor having a resonance reflectance spectrum with a central resonance wavelength and a resonance linewidth. The method includes reflecting broadband light having a spectral bandwidth greater than the RWG biosensor resonance linewidth from the at least one RWG biosensor to generate resonantly reflected light. The method also includes passing the resonantly reflected light through a tunable wavelength filter having a transmittance spectrum with a central wavelength while adjusting the central wavelength over a wavelength range to form filtered resonantly reflected light. The method additionally includes detecting the filtered resonantly reflected light to form an electrical signal representative of the central resonance wavelength. The method also includes determining the central resonant wavelength of the at least one RWG biosensor from the electrical signal.

These and other aspects of the disclosure will be further understood and appreciated by those skilled in the art by reference to the following written specification, claims and appended drawings.

BRIEF DESCRIPTION OF THE DRAWINGS

A more complete understanding of the present disclosure may be had by reference to the following detailed description when taken in conjunction with the accompanying drawings, wherein.

DETAILED DESCRIPTION

Reference is now made to embodiments of the disclosure, exemplary embodiments of which are illustrated in the accompanying drawings.

The claims as set forth below constitute part of this Detailed Description and are incorporated into this section by reference.

Figure 1:
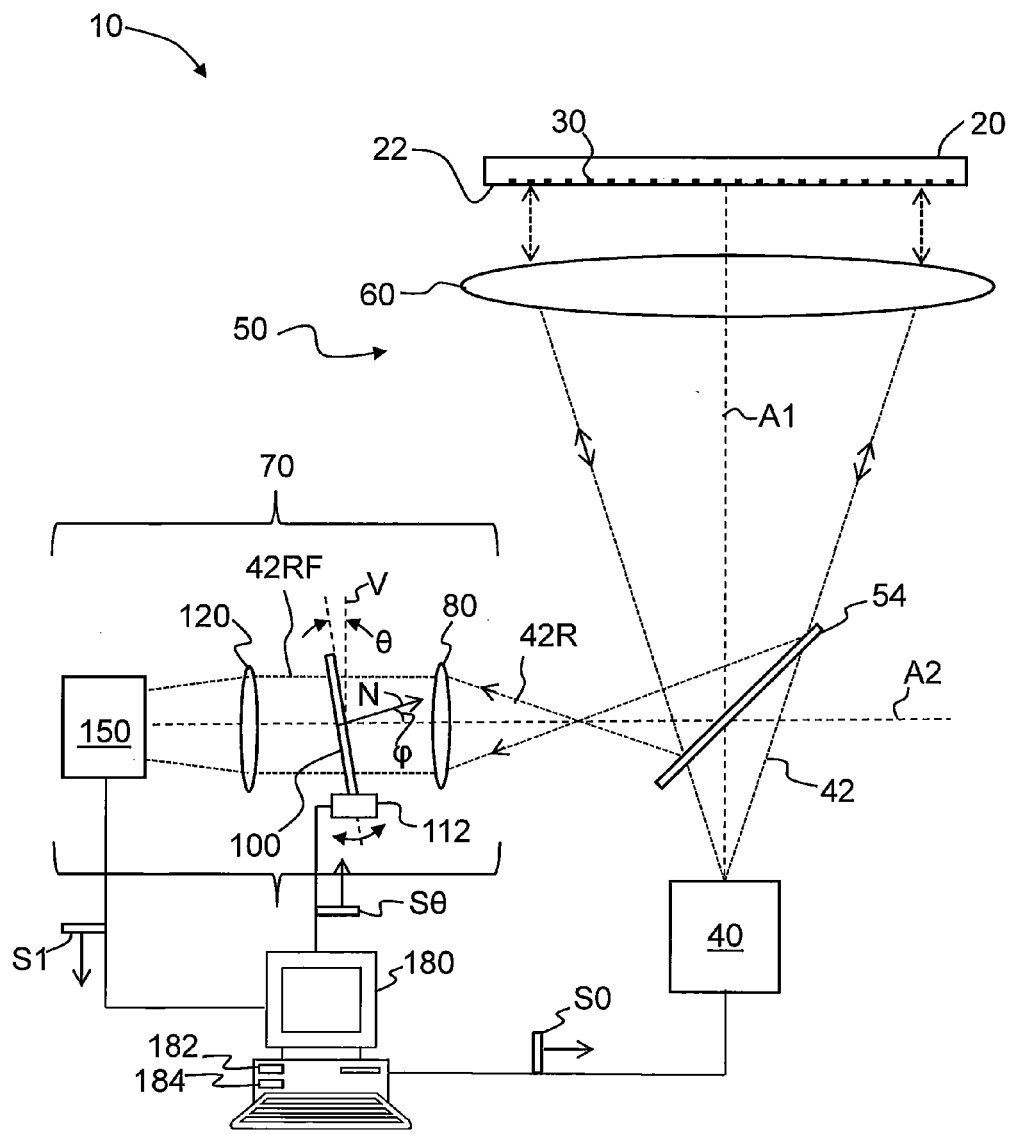
FIG. 1 is a schematic diagram of an example label-independent optical reader that includes the wavelength-tunable detector as disclosed herein.

FIG. 1 is a schematic diagram of an example optical reader system ("system") 10 according to the disclosure. System 10 includes a microplate 20 having a front surface 22 that operably supports an array of resonant waveguide (RWG) biosensors 30. RWG biosensor 30 has a resonance reflectance spectrum $RS_{30}$ with a resonance linewidth $\Delta\lambda_{30}$ and a center wavelength ("center resonance wavelength") $\lambda_C$. In an example embodiment, the resonance linewidth $\Delta\lambda_{30}$ is about 0.8 nm measured at full-width half maximum. System 10 is configured to "read" (i.e., determine) one or more center resonance wavelengths $\lambda_C$ for a corresponding one or more RWG biosensors 30.

In the example configuration of system 10 of FIG. 1, microplate front surface 22 is substantially normal to an axis A1, along which resides a broadband light source 40. An example broadband light source 40 includes a superluminescent diode (SLD), as available from Superlum Diodes, Ltd., Moscow, Russia. An example SLD light source has a spectral bandwidth of 20 nm and center wavelength of about 840 nm. A conventional broadband LED can also be used as broadband source 40. In embodiments, broadband light source 40 has a spectral bandwidth $\Delta\lambda_{40}$ in the range from 10 nm to 60 nm.

System 10 also includes an optical system 50 shown by way of example as consisting of a beam splitter 54 disposed along axis A1 and adjacent broadband light source 40, and an objective lens 60 adjacent microplate 20. Beam splitter 54 can be in the form of a partially reflecting mirror. Beam splitter 54 defines an axis A2 that in an example is substantially at a right angle to axis A1.

System 10 also includes along axis A2 a wavelength-tunable detector 70. An example wavelength-tunable detector 70 includes, in order along axis A2 from beam splitter 54: a collimating lens 80, a tunable wavelength filter 100, an imaging lens 120, and a photodetector 150. Photodetector 150 may include, for example, a CCD or CMOS digital camera. Example tunable wavelength filters 100 include a monochromator with an adjustable (e.g., motorized) diffraction grating, a tunable Fabry-Perot etalon that employs actuators (e.g., piezoelectric or MEMS actuators), a liquid crystal tunable filter, an acousto-optic tunable filter, and an angle-adjustable Fabry-Perot etalon. Of these example tunable wavelength filters, the angle-adjustable embodiment provides a good balance of performance and cost, and is the one illustrated in FIG. 1 by way of example.

Tunable wavelength filter 100 has a transmittance spectrum $TS_{100}$ (see FIG. 2A, introduced and discussed below) with a spectral (transmittance) bandwidth $\Delta\lambda_{100}$ centered on a center wavelength $\lambda_{CT}$. The "tunability" of tunable wavelength filter 100 refers to its ability to adjust its central wavelength $\lambda_{CT}$ while maintaining its spectral bandwidth $\Delta\lambda_{100}$ substantially constant and relatively narrow, e.g., substantially the same as the resonance linewidth $\Delta\lambda_{30}$ of RWG biosensor 30.

Thus, the transmission function spectrum $TS_{100}$ of tunable filter 100 essentially shifts unchanged with wavelength as the central wavelength $\lambda_{CT}$ changes within a tunable center-wavelength range. Tunable wavelength filter 100 makes an angle θ ("filter angle") relative to the vertical, which is denoted by dashed line V. It is noted that the filter angle θ is the same as the angle φ formed by axis A2 and the surface normal N to the tunable wavelength filter.

In an example, tunable filter 100 is supported by a filter support device 112 that in one example is adapted to adjust the orientation of the filter (i.e., filter angle θ). In an example, filter angle θ is adjustable between about 4° and 19° to sweep the center wavelength $\lambda_{CT}$ over about 24 nm (e.g., from 820 nm to 844 nm). The tunable wavelength filter 100 is thus angle-adjustable relative to resonantly reflected broadband light 42R incident thereon and that in an example travels generally parallel to axis A2.

The spectral bandwidth $\Delta\lambda_{100}$ of tunable wavelength filter 100 is preferably selected for optimum resolution in detecting the center resonance wavelength $\lambda_C$ of RWG biosensor 30. A wide spectral bandwidth $\Delta\lambda_{100}$ increases the total optical power transmitted, but filters high-frequency components from the resonance reflectance spectrum $RS_{30}$, which may reduce the detection sensitivity. The significant high-frequency components of the resonance reflectance spectrum $RS_{30}$ are preserved if the spectral bandwidth $\Delta\lambda_{100}$ is substantially the same as the resonance linewidth $\Delta\lambda_{30}$ or narrower. Greater widths can be tolerated with slightly reduced performance, provided that the transmittance spectrum $TS_{100}$ falls within the wavelength range for which both broadband light source 40 has substantially uniform intensity and photodetector 150 has a substantially uniform detection capability.

In contrast, a very narrow spectral bandwidth $\Delta\lambda_{100}$ does not filter significant high-frequency components of the resonance reflectance spectrum $RS_{30}$ but may not transmit sufficient light for detection. Decreasing the spectral bandwidth $\Delta\lambda_{100}$ calls for an approximately proportional increase of either the illumination intensity or detector area to maintain the same signal level An example spectral bandwidth $\Delta\lambda_{100}$ is from 0.01 nm to 8 nm.

System 10 also includes a controller 180 having a processor unit ("processor") 182 and a memory unit ("memory") 184. Controller is operably connected to broadband light source 40, tunable wavelength filter support device 112, and photodetector 150, and controls the operation of these devices via respective control signals S0, Sθ and S1 in controlling the overall operation of system 10. Example processors 182 can include, for example, a computer, microprocessor, one or more central-processing units (CPU), a field-programmable gate array (FPGA), and like devices. Memory 184 can be any type of digital memory used in computers, such as solid-state memory, magnetic memory, and optical memory.

In the operation of system 10, broadband light source 40 emits broadband light 42 that travels along axis A1 as a diverging light beam. Broadband light 42 passes thorough beam splitter 50 and is collimated by objective lens 60 to be substantially normally incident upon biosensors 30 supported by microplate 20. The substantially collimated broadband light 42 is resonantly reflected by one or more RWG biosensors 30 to form resonantly reflected light 42R having center resonance wavelength $\lambda_C$. Resonantly reflected light 42R travels back to objective lens 60, which now forms a converging resonantly reflected light beam, which is reflected by beam splitter 50 to travel along axis A2.

Optical system 50 is thus generally configured to direct broadband light 42 to the at least one RWG sensor 30 to form the resonantly reflected light 42R, and direct the resonantly reflected light to the wavelength-tunable detector 70. Other configurations for optical system 50 beyond the disclosed exemplary embodiments can be employed.

Resonantly reflected light 42R is received and is substantially collimated by collimating lens 80. The substantially collimated reflected light 42R then travels through tunable wavelength filter 100, which has the aforementioned central wavelength $\lambda_{CT}$ and a narrow spectral (transmission) bandwidth $\Delta\lambda_{100}$. This filtered resonantly reflected light, denoted 42RF, is then imaged by imaging lens 120 onto photodetector 150, which converts the imaged filtered light 42RF into an electronic image signal S1, which is sent to controller 180. In an example, imaging lens 120 forms an image of RWG biosensor(s) 30 on photodetector 150.

If multiple RWG biosensors 30 are illuminated, resonantly reflected light can include all of the center resonant wavelengths associated therewith. The formation of an image of the RWG biosensors 30 on photodetector 150 allows for each RWG biosensor to be imaged onto corresponding regions of the photodetector. The electrical signal S1 includes information from each of the photodetector regions (i.e., a subset of the photodetector pixels) so that each RWG biosensor 30 can be read and its corresponding central resonance wavelength determined. Thus, the digital image formed by photodetector 150 can be considered as including a number of sub-images corresponding to the different RWG biosensors. Likewise, the digital image can be considered to consist of a series of digital images, one for each of a number of different center wavelengths $\lambda_{CT}$ generated by adjusting tunable wavelength filter 100. Electrical signal S1 can therefore be considered to include this series of digital images.

Thus, controller 180 receives electrical signal S1 from photodetector and stores it in memory 184. Processor 182 analyzes the digital image embodied in pre-processed electrical signals S1 based on instructions (e.g., image-processing software) stored therein or in memory 182. Controller 180 is configured (e.g., processor 182 is programmed or operates under the control of software stored in memory 184) to determine if there are any changes (e.g., 1 part per million) in the RWG biosensor refractive index (for each RWG biosensor 30 measured) caused by the presence of, for example, a biological substance or a change in the substance, within about 150 to 200 nm from the biosensor surface.

Figure 2A:
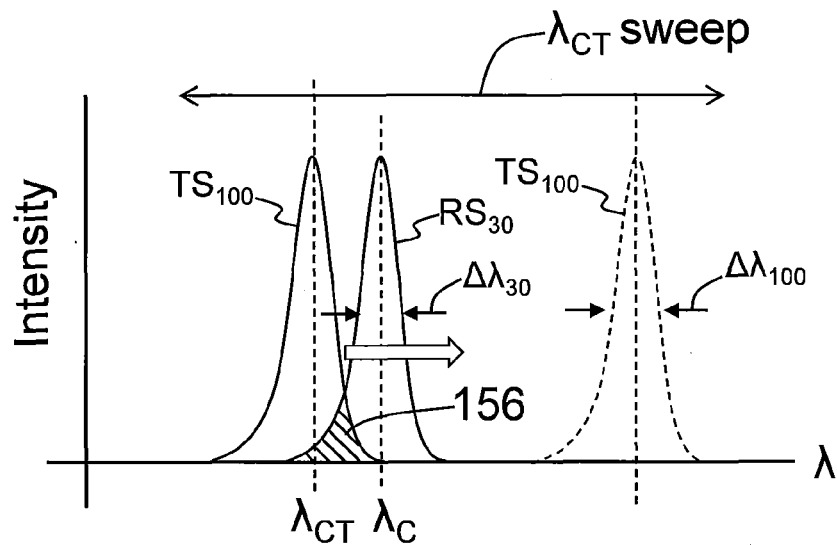
FIG. 2A is a plot of wavelength vs. intensity and shows the transmittance spectrum $TS_{100}$ of the tunable wavelength filter and the reflectance spectrum $RS_{30}$ of an example biosensor, illustrating how the central wavelength of the transmittance spectrum sweeps over a wavelength range relative to the biosensor resonance reflectance spectrum.

FIG. 2A is a plot of wavelength vs. intensity and shows the transmittance spectrum $TS_{100}$ of tunable wavelength filter 100 and the biosensor reflectance spectrum $RS_{30}$ for a given RWG biosensor 30. For a generally flat output spectrum of broadband light source 40, the response at photodetector 150 is proportional to the overlapping area 156 between the transmittance spectrum $TS_{100}$ of tunable wavelength filter 100 and the biosensor reflectance spectrum $RS_{30}$.

Center wavelength $\lambda_{CT}$ of tunable wavelength filter 100 is adjusted, i.e., swept, as indicated by the double-ended arrow in FIG. 2A. This is accomplished by changing the filter angle $\theta$, e.g., control signals S$\theta$ from controller 180. Photodetector 150 then detects the resulting resonantly reflected filtered light 42RF for each center wavelength $\lambda_{CT}$ and in response generates the aforementioned electrical signal S1.

The electrical signal S1 is used to generate a detected spectrum $DS_{150}$ having a center wavelength that is substantially the same a center resonance wavelength $\lambda_C$ of biosensor resonance reflectance spectrum $RS_{30}$. Detected spectrum $DS_{150}$ is a convolution of the transmittance spectrum $TS_{100}$ of tunable wavelength filter 100 and the biosensor reflectance spectrum $RS_{30}$ as a function of the center wavelength $\lambda_{CT}$ of the tunable wavelength filter, as described in U.S. 2011/0109909.

Figure 2B:
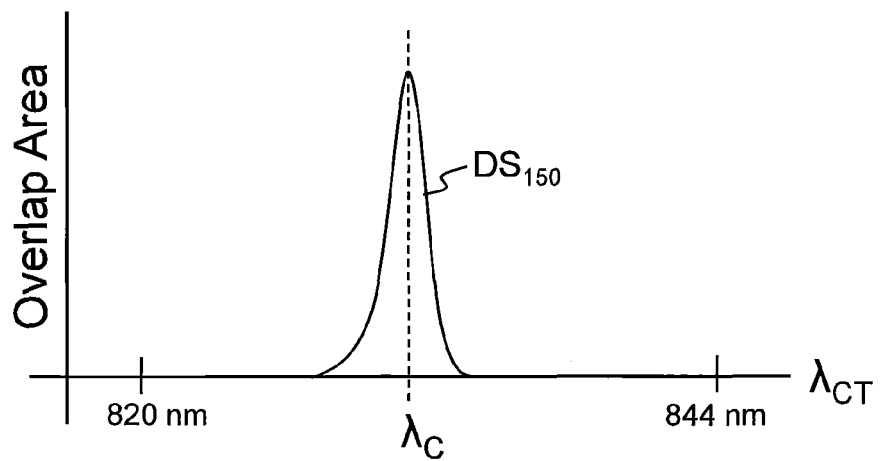
FIG. 2B plots the overlap area of the transmittance spectrum $TS_{100}$ of the tunable wavelength filter and the resonance reflectance spectrum $RS_{30}$ of a biosensor as a function of the central wavelength of the tunable wavelength filter, illustrating how the resulting detector spectrum has the central resonance wavelength of the RWG biosensor.

An example (schematic) detected spectrum $DS_{150}$ is illustrated in FIG. 2B, which shows a plot of the overlap area 156 of FIG. 2A vs. center wavelength $\lambda_{CT}$ of tunable wavelength filter 100. Center wavelength $\lambda_{CT}$ is shown in FIG. 2B as having been swept (adjusted) over a wavelength range of from 820 nm to 844 nm. Information about detected spectrum $DS_{150}$ and the biosensor reflectance spectrum center wavelength $\lambda_C$ is embodied in electrical signal S1, so that controller 180 can be used to extract spectrum $DS_{150}$ and center wavelength $\lambda_C$ from the electrical signal.

Figure 3:
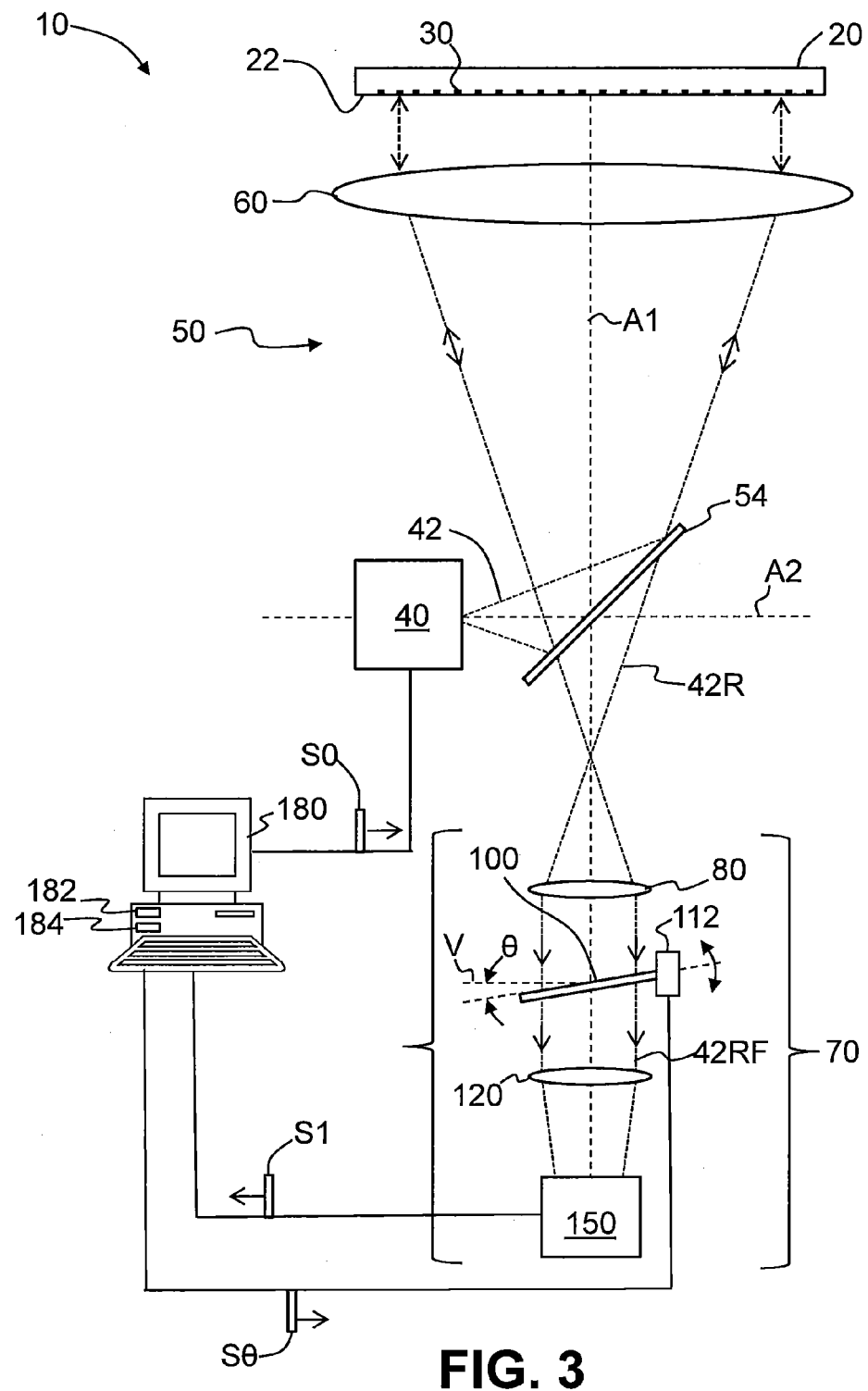
FIG. 3 is a schematic diagram similar to FIG. 1 that illustrates an alternate configuration of the label-independent optical reader wherein the wavelength-tunable detector and the microplate lie along the same axis.

FIG. 3 is similar to FIG. 1 and illustrates an example embodiment of system 10 wherein the broadband light source 40 lies along axis A2 and tunable wavelength detector 70 is disposed along axis A1. The operation of system 10 of FIG. 3 is essentially the same as that of FIG. 1, except that now broadband light 42 is reflected by beam splitter 50 so that it travels along axis A1 to objective lens 60 and to RWG biosensors 30. The resonantly reflected light 42R is then transmitted by beamsplitter 50 so that it continues traveling along axis A1 to tunable wavelength detector 70.

Other configurations for system 10 that are consistent with the spirit of the example embodiments described above can be employed. For example, the broadband light 42 can be made incident at an angle relative to microplate surface 22 and the resonantly reflected light can be collected at the corresponding reflection angle by wavelength-tunable detector 70. Optical system 50 can be configured to facilitate this non-normal-incidence configuration.

Thus, it will thus be apparent to those skilled in the art that various modifications to the preferred embodiment of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. A wavelength-tunable detector for measuring a center resonance wavelength of at least one RWG biosensor having a center resonance wavelength and illuminated with broadband light, comprising:
    a tunable wavelength filter having a tunable center wavelength within a tunable center-wavelength range, and a transmission spectrum with a spectral bandwidth narrower than the tunable center-wavelength range, the tunable wavelength filter being arranged to receive and filter the resonantly reflected broadband light to form filtered resonantly reflected light as the tunable center wavelength is adjusted; and
    a photodetector arranged to receive the filtered resonantly reflected light and to generate an electrical signal representative of a detected spectrum as a function the tunable center wavelength, wherein the detected spectrum has a center wavelength substantially the same as the RWG biosensor center resonance wavelength.

2. The wavelength-tunable detector of claim 1, wherein the RWG biosensor has a resonance linewidth, and wherein the spectral bandwidth of the tunable wavelength filter is substantially the same as the RWG biosensor resonance linewidth.

3. The wavelength-tunable detector of claim 1, wherein the tunable wavelength filter is angle-adjustable relative to resonantly reflected broadband light incident thereon.

4. The wavelength-tunable detector of claim 1, further comprising a collimating lens operably disposed adjacent the tunable wavelength filter to receive and collimate the resonantly reflected light and to direct the collimated resonantly reflected light to the tunable wavelength filter.

5. The wavelength-tunable detector of claim 4, further comprising an imaging lens operably arranged to receive the filtered resonantly reflected light and form on the photodetector an image of the at least one RWG biosensor.

6. The wavelength-tunable detector of claim 1, further comprising a controller adapted to receive and process the electrical signal to determine the center resonance wavelength of the at least one RWG biosensor.

7. The wavelength-tunable detector of claim 1, wherein the photodetector comprises a CMOS camera or a CCD camera.

8. The method of claim 1, wherein the tunable center-wavelength range is from about 820 nm to about 844 nm.

9. A label-independent optical reader for reading at least one RWG biosensor supported by a microplate, comprising:
    the wavelength-tunable detector of claim 1;
    a broadband light source that emits the broadband light;
    an optical system configured to direct the broadband light to the at least one RWG sensor to form the resonantly reflected light, and to direct the resonantly reflected light to the wavelength-tunable detector; and a controller adapted to receive and process the electrical signal from the photodetector to determine the center resonance wavelength of the at least one RWG biosensor.

10. The label-independent optical reader of claim 9, wherein the broadband light source comprises a superluminous diode (SLD) or a light-emitting diode (LED).

11. The label-independent optical reader of claim 9, wherein the broadband light source and the microplate lie along a same axis.

12. The label-independent optical reader of claim 9, wherein the RWG biosensor has a resonance linewidth, and wherein the spectral bandwidth of the tunable wavelength filter is substantially the same as the RWG biosensor resonance linewidth.

13. A method of reading at least one resonant waveguide grating (RWG) biosensor having a resonance reflectance spectrum with a central resonance wavelength and a resonance linewidth, comprising:
 reflecting broadband light having a spectral bandwidth greater than the RWG biosensor resonance linewidth from the at least one RWG biosensor to generate resonantly reflected light;
 passing the resonantly reflected light through a tunable wavelength filter having a transmittance spectrum with a central wavelength while adjusting the central wavelength over a tunable center-wavelength range to form filtered resonantly reflected light;
 detecting the filtered resonantly reflected light to form an electrical signal representative of the central resonance wavelength; and
 determining the central resonant wavelength of the at least one RWG biosensor from the electrical signal.

14. The method of claim 13, wherein adjusting the central wavelength of the tunable wavelength filter further comprises changing a filter angle relative to the resonantly reflected light passing therethrough.

15. The method of claim 14, further comprising supporting the tunable wavelength filter in a filter support device and adjusting the filter angle by a control signal provided to the filter support device.

16. The method of claim 13, wherein the filter angle is in the range from about 4° to about 19°.

17. The method of claim 13, further comprising:
 forming an image on the photodetector with the filtered resonantly reflected light, wherein the image includes multiple images of corresponding multiple RWG biosensors for each of a plurality of different center wavelengths of the tunable wavelength filter; and
 processing the electrical signal to determine the center wavelengths of each of the multiple RWG biosensors, wherein the electrical signal is representative of the multiple images.

18. The method of claim 13, wherein the resonantly reflected light that passes through the tunable wavelength filter is substantially collimated.

19. The method of claim 13, wherein the wavelength range of the central wavelength of the tunable wavelength filter is from about 820 nm to about 844 nm.

20. The method of claim 13, wherein the at least one RWG biosensor constitutes a plurality of biosensors operably supported by a microplate.

* * * * *